Feb. 11, 1941. F. H. HOWARD Plant Pat. 449
ROSE PLANT
Filed July 31, 1940
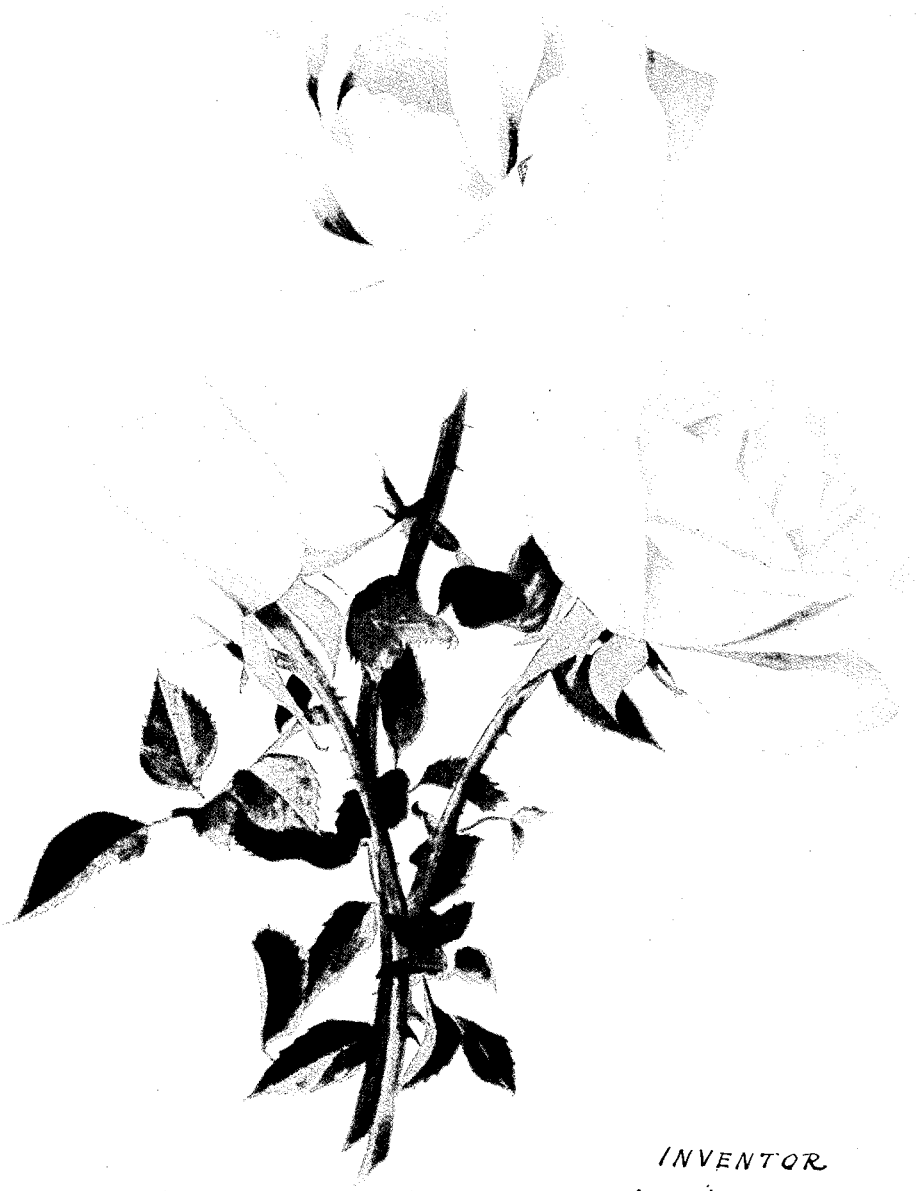
INVENTOR
Frederick Huber Howard
By Orville M. Kile.
Plant Patent Agt.

Patented Feb. 11, 1941

Plant Pat. 449

UNITED STATES PATENT OFFICE

449

ROSE PLANT

Frederick Huber Howard, Montebello, Calif.

Application July 31, 1940, Serial No. 348,973

1 Claim. (Cl. 47—61)

My present invention relates to improvements in hybrid tea roses and is a cross between the varieties Miss Rowena Thom and Lady Forteviot, the latter being the seed parent. This variety is the result of many experiments carried on by me in my greenhouses and gardens.

This new variety is exceptionally vigorous in its growth and freely produces very large, bi-color flowers. The color of the open rose is a deeper and richer gold than any other rose known to me. The flowers are enormous and are of a pleasing high-centered form which is retained.

The variety has been asexually reproduced for several generations and its characteristics have proved to be permanently fixed.

The original illustrations accompanying this application show in approximately true colors and only slightly smaller than the usual size, three specimens of this new variety in various stages of opening.

Following is a detailed description of this variety. Reference is made to Ridgway's Color Standards and Nomenclature, except where it is obvious that the ordinary dictionary color term is intended.

*The plant*

Growth: Very vigorous, upright bush, somewhat spreading; about 4 feet in height. Breaks freely on flowering stems.

Blooming habit: Profuse bloomer, producing heavy succession of bloom throughout the season.

Stems: Heavy; straight; very strong and stiff; Olive Green (Plate IV) with considerable overlay of Hydrangea Red (Plate XXVII) to Cameo Brown (Plate XXVIII). A noticeable feature of these stems is the prominence of the leaf buds at the nodes.

Thorns: Numerous; very large; sharp; downward-pointing; Neutral Red (Plate XXXVIII).

Foliage: Abundant; healthy; high on stem; compound, usually with three to five leaflets.

*Leaflets.*—*Size*—relatively small compared to size of blossom. Terminal leaflet averages about 2 inches long by 1½ inches wide. *Shape*—ovate with acuminate apex and rounded base. *Margin*—finely and sharply serrated. *Color*—approximately Elm Green (Plate XVII), on the upper surface. Under surface much lighter green, with occasional slight reddish tinge. *Aspect*—glossy and waxy.

Rachis: Medium; grooved above; smooth on under side except for several sharp hooked thorns.

Stipules: Medium in length; narrow; clinging; points acute and long; extend almost to first leaflet, the stem of the rachis being very short.

*The flower*

Bud:

*Shape.*—Long ovoid.

*Size.*—Very large; sometimes 2½ inches long.

*Color.*—The tight bud is various tones of dull red, the predominating tones being from Jasper Red to Eugenia Red (Plate XIII), with an aiglet of Light Cadmium (Plate IV) which suffuses upward. Opening bud is the same at the base but the upper portion of the petals tends more toward Spinel Pink and Thulite Pink (Plate XXVI).

*Peduncle.*—Short; strong; stiff; either straight or gracefully curved; covered with numerous small sharp thorns; usually much redder than the stems, both thorns and peduncle having a very heavy overlay of approximately Deep Hellebore Red (Plate XXXVIII).

*Sepals.*—Medium in length; slight tendency to foliaceousness on one or two sepals of each blossom; frequently have side appendages at base; outside surface Cedar Green (Plate VI) frequently tinged with dark red.

Blossom:

*Borne.*—Singly.

*Size.*—Very large; under most favorable conditions attains six inches in diameter.

*Form.*—Globular, with very high center. As the flowers open they become loose but hold their shape exceptionally well. Stamens and pistils are not visible until the very mature stage is reached.

*Petalage.*—Double; 30 to 40 petals in June in my gardens.

*Color.*—As the flower begins to open, the bi-color effect becomes evident, the inner surface of the petals being between Capucine Orange (Plate III) and Apricot Orange (Plate XIV) on their upper edge, with a large aiglet of Light Cadmium (Plate IV) which merges into it. This gives an effect commonly spoken of as "ruddy gold." The outer surface, particularly of the inner petals, is of glowing Old Rose (Plate XIII) suffused with Light Cadmium (Plate IV) which extends upward from the large aiglet. Very little of the outer surface of the petals is visible in the open rose. In the fully opened flower the petals are lighter in tone on both petal surfaces.

Fragrance: Penetrating tea odor.

Longevity: Exceptionally long-lasting.

Behavior: Petals drop off cleanly.

Petals:

*Shape.*—Almost round and deeply cupped. Edges—often deeply scalloped and cut. Roll back slightly.

*Aspect.*—Silky.

*Texture.*—Very heavy.

*Size.*—Unusually large, being from 2½ to 3 inches in both axial and transverse measurements.

Reproductive organs:

*Pistils.*—Many; bunched in center of flower. *Styles*—medium length; Pale Green Yellow (Plate V). *Stigmas*—approximately Naples Yellow (Plate XVI).

*Stamens.*—A large number; surround bunched pistils. Filaments—varying lengths but longer than pistils; slender; approximately Empire Yellow (Plate IV). *Anthers*—large; approximately Cadmium Yellow (Plate III).

*Ovaries.*—Very large; walls thick and fleshy; inclosed in calyx.

Having thus disclosed my invention, I claim:

A new and distinct variety of hybrid tea rose plant, characterized particularly by its very vigorous growth; its free blooming habit; its abundant, healthy foliage; and its very large buds and blossoms of high-centered and lasting form, penetrating tea fragrance and distinctive bi-color combination predominantly a deep ruddy gold with outer surface of petals principally tones of pink and rose, substantially as shown and described.

FREDERICK HUBER HOWARD.